United States Patent
Taylor et al.

(10) Patent No.: US 6,609,411 B1
(45) Date of Patent: Aug. 26, 2003

(54) APPARATUS FOR REMOVING WATER FROM DIELECTRIC OIL IN ELECTRICAL POWER TRANSFORMERS

(75) Inventors: Benjamin G. Taylor, Colorado Springs, CO (US); Jeffrey J. Baltes, Colorado Springs, CO (US)

(73) Assignee: Velcon Filters, Inc., Colorado Springs, CO (US)

( * ) Notice: Subject to any disclaimer, the term of this patent is extended or adjusted under 35 U.S.C. 154(b) by 0 days.

(21) Appl. No.: 09/913,481

(22) PCT Filed: Feb. 29, 2000

(86) PCT No.: PCT/US00/05149
§ 371 (c)(1),
(2), (4) Date: Aug. 14, 2001

(87) PCT Pub. No.: WO00/52445
PCT Pub. Date: Sep. 8, 2000

Related U.S. Application Data
(60) Provisional application No. 60/122,909, filed on Mar. 5, 1999.

(51) Int. Cl.$^7$ ................................................. G01N 1/00
(52) U.S. Cl. ................................................. 73/19.11
(58) Field of Search ....................... 73/19.11, 19.1, 73/61.41, 61.43; 324/664, 689, 694, 698; 340/646; 95/247, 266

(56) References Cited

U.S. PATENT DOCUMENTS

| | | |
|---|---|---|
| 3,844,160 A | 10/1974 | Yamaoka |
| 3,998,738 A | 12/1976 | Kusay |
| 5,574,214 A | 11/1996 | Balton et al. |
| 5,691,706 A | 11/1997 | Butler et al. |

*Primary Examiner*—Robert Raevis
(74) *Attorney, Agent, or Firm*—Donald R. Fraser

(57) ABSTRACT

An apparatus for removing water from a dielectric oil which includes a vacuum pump (56) which militates against the introduction of air into the dielectric oil and a thin film capacitance sensor (48) for monitoring the amount of moisture present in the dielectric oil.

8 Claims, 1 Drawing Sheet

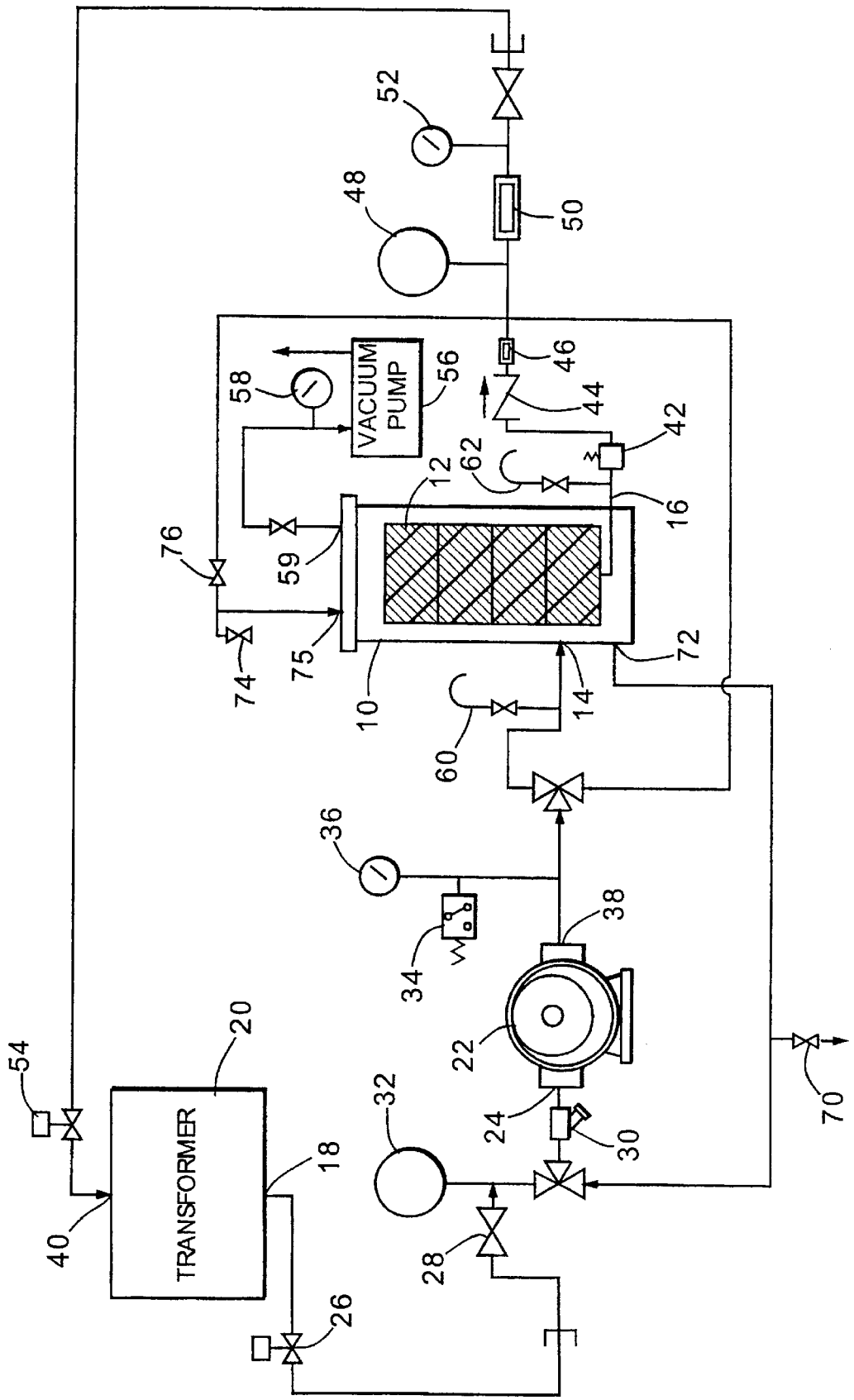

APPARATUS FOR REMOVING WATER FROM DIELECTRIC OIL IN ELECTRICAL POWER TRANSFORMERS

This is a continuation of provisional patent application Ser. No. 60/122,909 filed Mar. 5, 1999.

FIELD OF THE INVENTION

This invention relates to an apparatus for drying dielectric oils and more particularly to an apparatus for removing water from dielectric oil used in electrical power transformers.

BACKGROUND OF THE INVENTION

A key component in delivering electrical energy to the consumer is the dielectric oil-filled power transformer. Electricity is typically generated at some location distant from the point of consumption. To deliver it economically, the voltage from the generator is increased to higher levels by step-up transformers for transmission to a number of sub-stations where step-down transformers reduce the voltage for industrial and municipal use. Electricity is distributed at even lower voltages for domestic use. Transformers are critical links in the delivery of power from the source to the consumer in an economical and reliable fashion. Small power transformers are typically mounted on utility poles positioned along streets, at malls, and industrial sites, whereas moderate to large size units are located at substations and generating stations.

Transformers are primarily composed of conductors that may be copper or aluminum, and insulating materials that are typically mineral oil and paper. The mineral oil serves two functions: 1) as a coolant to minimize overheating of the transformer, and 2) as a dielectric providing sufficient strength to prevent dielectric breakdown between conducting parts at different electrical potentials and also between the energized parts and the grounded tank. The paper serves as an electrical insulator and provides mechanical support for the electrical conductor packages. A large transformer may contain 30,000 gal (113 550 L) of dielectric oil and 30,000 lbs (13 610 kg) of paper insulation.

Transformer insulating materials such as mineral oil and paper must be properly dried during the manufacturing process. A certain degree of dryness must then be maintained during the service life of the unit.

In order for the transformer to operate properly, the insulating materials must be dried to a proper level. The dielectric breakdown voltage of oil is reduced with increasing water content. As dielectric breakdown voltage is also affected by the presence of particles, it can not be used to predict the water content.

Oil is typically dried to less than 10 ppm water by weight and can increase to 20–30 ppm in use depending upon the voltage class of the equipment. A worst case situation arises when the water content, even at low parts per million, becomes greater than that required for saturation of the oil, and free water is formed. This results in drastically-reduced dielectric breakdown strength of the oil with the risk of failure of the transformer greatly increased.

The paper insulation must also be free of water to achieve good dielectric properties and enhance resistance to degradation. The concentration of water is usually between 0.1 to 0.5% by weight. The quantities of water in the paper insulation is much greater than that in the oil. When oil and paper are together, water will partition between them primarily based upon temperature.

As more demand or load is placed on a transformer, the insulating materials increase in temperature. The elevation in temperature forces water from the paper insulation into the dielectric oil. As demand is reduced and the transformer cools, the water migrates from the oil to the paper.

The paper must remain in a relatively dry state to prevent excessive water from being driven into the oil at hotter temperatures. It is actually during the cooling cycle that the water will exceed saturation in the oil, creating a problem.

The key to preventing failures in transformers from excessive water is proper monitoring.

A crucial step in obtaining reliable water measurements is acquiring a representative oil sample.

Transformers are tested at the factory to ensure drying procedures are adequate. Testing of dew point, vapor pressure, and electrical properties are used to assess the water content of the paper insulation before the transformer is filled with oil. Measurement of water in the oil is performed during and after filling of the transformer. In some cases the transformer may be shipped with dry air or nitrogen under slight positive pressure and then oil filled in the field.

Once the transformer is filled with oil, it is extremely difficult and almost impossible, for practical purposes, to obtain paper samples. Therefore, evaluation of the dryness of the paper insulation is performed by external overall measurement of the electrical properties of the transformer winding insulations that are influenced by water, or by taking samples of oil, recording the oil temperature, and using appropriate correlation curves to determine water content of the paper and dielectric oil. The latter can be effectively performed only if the transformer has been maintained at a steady warm temperature for many days to allow the system to come to a steady state.

Oil from transformers in the field should be checked for water content to make sure the manufacturer properly dried the paper insulation, to see if a leak has occurred, and because insulation degradation results in water formation over long periods of time. Careful monitoring can help prevent the conditions that will result in the formation of free water above the saturation level in oil and subsequent failure of a transformer. A margin of safety is provided by maintaining the insulation dry enough so that under all operating conditions, the water in oil is at less than 50% saturation.

Presently, in order to effect the desired dehydration of the dielectric oil in an energized operating transformer involves a process wherein the transformer containing wet dielectric oil must be taken out of service. The dielectric oil is removed from the transformer and is serviced by heating the oil above about 200° F. under high vacuum to remove built-up dissolved water. This is generally time consuming and accomplished by circulating the oil to be treated through a heating and evacuating system mounted on a mobile service truck. For large transformers, the drying process may require several attendants overseeing the removal, working in twelve hour shifts for a period of one week.

It is an object of the present invention to produce an apparatus for removing water from the dielectric oil in an energized electrical power transformer while the transformer is in service.

Another object of the invention is to produce an apparatus for removing water from the dielectric oil in an energized electrical power transformer including the vacuum pump for militating against air entering the transformer during the period the water is being removed from the dielectric oil.

Still another object of the invention is to produce an apparatus for removing water from the dielectric oil of an energized transformer including a monitor for sensing the water content of the dielectric oil before and after the oil is caused to be passed through the treating filter cartridges in the evacuated filter housing or vessel.

SUMMARY OF THE INVENTION

The above, as well as other objects of the invention, may be readily achieved by an apparatus for removing water from the dielectric oil in an electrical power transformer comprising: a pump for circulating the dielectric oil from a transformer and returning the same to the transformer; a filter in fluid communication with the pump for removing water from the dielectric oil; a vacuum pump in fluid communication with the filter for preventing air from being introduced into the transformer; and a sensor for monitoring the dryness of the oil after circulation through the filter.

BRIEF DESCRIPTION OF THE DRAWINGS

The above, as well as other objects, features, and advantages of the present invention, will be understood from the detailed description of the preferred embodiment of the present invention when considered in the light of the accompanying drawing, in which:

FIG. 1 is a schematic illustration of the apparatus constructed in accordance with the invention.

DETAILED DESCRIPTION OF THE ILLUSTRATED EMBODIMENT

Referring now to the drawing, there is shown an apparatus for removing water from electrical power transformers incorporating the features of the invention. The apparatus includes a filter vessel 10 containing filter cartridges 12 through which the transformer oil to be treated is caused to flow. The filter vessel 10 is typically found of a welded carbon steel construction capsule of operating at a pressure of 100 psi. The vessel 10 is adapted to receive a number of the filter cartridges 12. Access to the interior of the filter vessel 10 is achieved through a hinged top cover, for example, fastened at the main portion of the vessel by bolts and eye nuts. No special tools are necessary to open the top cover. Suitable gasket means, such as for example a replaceable buna gasket, has been found to function satisfactorily under operating pressure conditions.

Also, it has been found that dissolved water may be satisfactorily removed from the dielectric transformer oil being treated by utilizing filter cartridges 12 available from Velcon Filters, Inc., Colorado Springs, Colo. sold under the trademark Superdri. These cartridges may be of the particular construction as illustrated and described in U.S. Pat. No. 5,574,214. The cartridges 12 are designed to remove dissolved water from insulating a dielectric oil used in electrical transformers and reduce the water in the oil to <10 ppm without the necessity of utilizing ancillary heat and vacuum.

The filter vessel 10 is provided with an oil inlet 14 and an oil outlet 16. The inlet 14 allows oil to be treated to enter the interior of the filter vessel 10 and pass through the individual cartridges 12 from the outside to the inside and the treated oil is then caused to exit the filter vessel 10 through the outlet 16.

The inlet 14 of the filter vessel 10 is in fluid communication with an oil outlet 18 of a transformer 20 through appropriate piping and an associated rotary gear pump 22. More specifically, it will be noted that the outlet 18 of the transformer 20 is connected to the inlet 24 of the pump 22. A normally open solenoid actuated valve 26 and a manual valve 28 are connected in the piping leading from the outlet 18 of the transformer 20. A strainer 30 may also be positioned in the line between the outlet 18 of the transformer 20 and the inlet 24 of the pump 22.

A water probe or sensor 32 may also be located in the line leading to the inlet 24 of the pump 22.

A pressure actuated switch 34 and a pressure gauge 36 may be disposed in the line between an outlet 38 of the pump 22 and the inlet 14 of the filter vessel 10.

The outlet side of the filter vessel 10 is coupled to the inlet side of the electrical transformer 20 through suitable piping. More specifically, the outlet 16 of the filter vessel 10 is in fluid communication with an inlet 40 of the transformer 20. The connecting piping includes a flow switch 42 capable of closing and thereby shutting off the system in the event the flow rate of the transient treated oil drops below a predetermined minimum flow rate of 0.5 gals./min., for example. Downstream of the flow switch 42 is a check valve 44, a sight glass 46, and a water probe or sensor 48 for sensing dissolved water in the same fashion as the sensor 32.

A flow meter 50 and a meter 52 for sensing the temperature of the treated dielectric oil are disposed in the line downstream of the sensor 48. Typically, the flow meter 50 is battery operated and is capable of reading the flow of the treated oil in gals./min. The temperature sensing meter 52 is normally capable of reading temperatures between 0° and 250° F.

Finally, a normally opened solenoid actuated valve 54 is in the input line to the transformer 20 and is capable of shutting down the system.

The filter vessel 10 is connected to a vacuum pump 56 having an associated vacuum gauge 58 through a suitable line from a separate outlet 59 of the filter vessel 10. The vacuum gauge 58 is typically capable of sensing a vacuum in inches of Hg. (30 in.Hg. –0 in.Hg.)

Sample ports 60 and 62 are disposed at the inlet and the outlet, respectively, to the filter vessel 10. The sample ports 60, 62 are employed to sample the oil entering and leaving the filter vessel 10, respectively.

The system may be provided with a manually operated drain for the system connected between a manually operated drain valve 70 and the outlet 18 of the transformer 20 and a separate outlet 72 of the filter vessel 10.

Also, the system is provided with a manually operated air vent valve 74 which is connected to an outlet 75 of the filter vessel 10. It will be observed that the air vent valve 74 is also selectively in communication with the remainder of the system through a manual control valve 76.

As a safety precaution, a double walled hydraulic hose line is preferred for use between the dielectric oil outlet 18 of the transformer 20 and the manual valve 28 leading to the inlet of the pump 22; and inlet 40 of the transformer 20 and the outlet 16 of the filter vessel 10 generally commencing downstream of the flow meter 50 and the temperature gauge 52.

In operation, after the inlets and outlets of the transformer 20 and the filter vessel 10 are properly coupled, the pump 22 and the vacuum pump 56 are energized from an associated electrical power source, not shown. With the solenoid actuated valves 26, 54 in the normally opened position, the wet dielectric oil is caused to be pumped from the transformer 20 to the filter vessel 10 by the pump 22. Simultaneously, the vacuum pump 56 draws a vacuum in the filter vessel 10 to eliminate air entering the system.

The wet oil entering the filter vessel 10 is caused to pass through the filter cartridges 12 which are effective to withdraw dissolved water from the transient oil. Thereafter, the treated dry oil is caused to be returned to the transformer 20 through the associated piping.

During the treating of the dielectric oil, the vacuum pump 56 is operative to militate against the presence of air in the system which would otherwise adversely effect the efficiency of the water removed from the transient oil.

From the foregoing description, one ordinarily skilled in the art can easily ascertain the essential characteristics of this invention and, without departing from the spirit and scope thereof, can make various changes and modifications to the invention to adapt it to various usages and conditions.

What is claimed is:

1. An apparatus for removing water from dielectric oil in an energized electrical power transformer comprising:

a pump for circulating the dielectric oil from a transformer and returning the dielectric oil to the transformer;

a filter in fluid communication with said pump for removing water from the dielectric oil;

a vacuum pump in fluid communication with said filter for preventing air from being introduced into the transformer; and a sensor for monitoring the dryness of the oil after circulation through said filter.

2. The apparatus for removing water from an energized electrical power transformer according to claim 1, further comprising a safety alarm for automatically isolating said pump for circulating the dielectric oil from the transformer in response to abnormal oil flow conditions.

3. The apparatus for removing water from an energized electrical power transformer according to claim 1, wherein said sensor is a thin film capacitance type.

4. The apparatus for removing water from an energized electrical power transformer according to claim 3, including a digital display for displaying the water content and the temperature of the dielectric oil.

5. The apparatus for removing water from an energized electrical power transformer according to claim 4, wherein said sensor includes at least one of an audible and a visual alarm energized when said sensor detects a water level in the dielectric oil that exceeds a preset level.

6. The apparatus for removing water from an energized electrical power transformer according to claim 1, wherein said filter includes first and second spaced apart electrically conductive walls, a bed of molecular sieves between the first and second walls, and a device for measuring the capacitance across the bed of molecular sieves between the first and second walls.

7. The apparatus for removing water from an energized electrical power transformer according to claim 1, including a co-axial hose interconnecting said pump for circulating the dielectric oil, said filter, and the transformer, wherein said co-axial hose includes a primary inner hose and a secondary outer hose.

8. The apparatus for removing water from an energized electrical power transformer according to claim 7, including a float alarm for monitoring the secondary outer hose of said co-axial hose.

\* \* \* \* \*